(12) United States Patent
Burak et al.

(10) Patent No.: US 10,890,141 B2
(45) Date of Patent: Jan. 12, 2021

(54) WATER INJECTION DEVICE, IN PARTICULAR OF AN INTERNAL COMBUSTION ENGINE, AND METHOD FOR OPERATING SUCH A WATER INJECTION DEVICE

(71) Applicant: Robert Bosch GmbH, Stuttgart (DE)

(72) Inventors: Ingmar Burak, Stuttgart (DE); Peter Schenk, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/473,789

(22) PCT Filed: Nov. 13, 2017

(86) PCT No.: PCT/EP2017/078989
§ 371 (c)(1),
(2) Date: Jun. 26, 2019

(87) PCT Pub. No.: WO2018/130321
PCT Pub. Date: Jul. 19, 2018

(65) Prior Publication Data
US 2019/0338731 A1 Nov. 7, 2019

(30) Foreign Application Priority Data

Jan. 10, 2017 (DE) .................. 10 2017 200 291

(51) Int. Cl.
*F02M 25/025* (2006.01)
*F02M 25/00* (2006.01)
(Continued)

(52) U.S. Cl.
CPC ...... *F02M 25/0227* (2013.01); *F02M 25/028* (2013.01); *G01F 23/2962* (2013.01);
(Continued)

(58) Field of Classification Search
CPC ...... F02M 25/025; F02M 25/00; F02D 19/12; F02D 41/2467
See application file for complete search history.

(56) References Cited

U.S. PATENT DOCUMENTS 6,666,084 B2 * 12/2003 Schelhas .............. G01F 9/008
73/290 R
9,217,352 B2 * 12/2015 Onodera .............. F01N 9/002
(Continued)

FOREIGN PATENT DOCUMENTS

CN 103003634 A 3/2013
CN 103728346 A 4/2014
(Continued)

OTHER PUBLICATIONS

International Search Report corresponding to PCT Application No. PCT/EP2017/078989, dated Jan. 19, 2018 (German and English language document) (7 pages).

*Primary Examiner* — Long T Tran
(74) *Attorney, Agent, or Firm* — Maginot, Moore & Beck LLP

(57) ABSTRACT

A water injection device, in particular of an internal combustion engine, includes a water tank for storing water, a conveying element connected to the water tank for conveying water, at least one water injector connected to the conveying element for injecting water, and a water quality and water fill level detection device for detecting a quality of the water in the water tank and a fill level of the water tank.

11 Claims, 4 Drawing Sheets

(51) Int. Cl.
*F02D 19/12* (2006.01)
*F02M 25/022* (2006.01)
*F02M 25/028* (2006.01)
*G01F 23/296* (2006.01)
*G01N 9/24* (2006.01)
*G01N 27/06* (2006.01)
*G01N 33/18* (2006.01)

(52) U.S. Cl.
CPC ............... *G01N 9/24* (2013.01); *G01N 27/06* (2013.01); *G01N 33/18* (2013.01)

(56) References Cited

U.S. PATENT DOCUMENTS

| | | | | |
|---|---|---|---|---|
| 2004/0255647 A1* | 12/2004 | Lin | ...................... | G01N 27/226 73/53.01 |
| 2008/0097679 A1* | 4/2008 | Keays | .................... | F02M 25/03 701/102 |
| 2011/0309087 A1* | 12/2011 | Hodgson | ............... | G01F 23/268 220/562 |
| 2012/0000185 A1* | 1/2012 | Narita | ................... | F01N 3/2066 60/274 |
| 2012/0000270 A1* | 1/2012 | Narita | ..................... | F01N 11/00 73/23.31 |
| 2012/0118059 A1 | 5/2012 | Reimer et al. | | |
| 2013/0219989 A1* | 8/2013 | Tarui | ...................... | G01N 27/22 73/23.31 |
| 2015/0160148 A1 | 6/2015 | Stanley | | |
| 2018/0023522 A1* | 1/2018 | Styles | ................. | F02D 41/0025 123/559.1 |

FOREIGN PATENT DOCUMENTS

| | | |
|---|---|---|
| DE | 10 2014 222 466 A1 | 5/2016 |
| EP | 1 266 668 A1 | 12/2002 |
| EP | 3 018 331 A1 | 5/2016 |
| JP | 2004-60539 A | 2/2004 |
| KR | 2016-96768 A | 8/2016 |
| WO | 2014/080266 A1 | 5/2014 |

* cited by examiner

WATER INJECTION DEVICE, IN PARTICULAR OF AN INTERNAL COMBUSTION ENGINE, AND METHOD FOR OPERATING SUCH A WATER INJECTION DEVICE

This application is a 35 U.S.C. § 371 National Stage Application of PCT/EP2017/078989, filed on Nov. 13, 2017, which claims the benefit of priority to Serial No. DE 10 2017 200 291.3, filed on Jan. 10, 2017 in Germany, the disclosures of which are incorporated herein by reference in their entirety.

The present disclosure concerns a water injection device of an internal combustion engine and such an internal combustion engine. Another aspect of the disclosure concerns a method for operating such a water injection device.

Due to increasing demands for reduced carbon dioxide emissions, internal combustion engines are increasingly being optimized in terms of fuel consumption. However, known internal combustion engines cannot be operated optimally in terms of consumption at high-load operating points, as the operation is limited by a tendency to knocking and high exhaust temperatures. One possible measure for reducing the tendency to knocking and reducing the exhaust temperatures is to inject water. There are usually separate water injection systems in place to allow water injection. For example, a water injection system for an internal combustion engine with exhaust gas recirculation, in which the water is injected into the mass flow of the exhaust gas recirculation, is known from WO 2014/080266 A1.

The water for the water injection can be provided from various sources. For example, it is possible for deionized water to be filled into a water tank by the driver. Another possibility is that the condensate from an evaporator of an air conditioning system is collected and processed. Alternatively, the exhaust condensate can be collected and processed. However, the supply of the water injection system in this way can be detrimental in terms of the quality of the water. For example, the driver can intentionally or inadvertently fill tap water with poor quality, such as water with too high a lime content. In addition, the condensate from the air conditioning system and the exhaust condensate may contain a high proportion of ions or have too low a pH.

SUMMARY

The water injection device according to the disclosure of an internal combustion engine, on the other hand, has the advantage of ensuring that only water of sufficient quality is used for water injection. Thus damage, especially due to corrosion, of the water-conveying components of the water injection device as well as impairments of the combustion of the internal combustion engine can be avoided. This is achieved according to the disclosure by a water injection device, in particular of an internal combustion engine, which uses a water tank for storing water, a conveying element for conveying water, whereby the conveying element is connected to the water tank, at least one water injector for injecting water that is connected to the conveying element and a water quality and water level detection device for detecting a quality of water in the water tank or the medium in the water tank, and a fill level of the water tank. Due to the water quality and water level detection device, the water quality and water level in the water tank can be determined before water injection is carried out. Thus, the proposed detection facility serves as a preventive measure against damage to the water injection device and a change of parameters relevant to flow and combustion.

The additional description, drawings, and features show preferred developments of the disclosure.

Preferably, the water quality and water level detection device includes an electrochemical sensor with two electrodes disposed in the water tank, wherein one electrode is provided with a capacitor. To detect the water quality, a conductivity of the water can be determined based on charging and discharging the capacitor. The electrodes with the capacitor preferably provide an "RC" circuit, with "R" indicating an electrical resistance between the electrodes and "C" indicating the capacitor. The conductivity is defined as the inverse value of the electrical resistance. From the measurement of voltage at the electrodes at a time after the beginning of the discharge, the electrical conductivity of the water between the electrodes can be concluded.

The electrodes are preferably disposed as close as possible to a lower region or bottom of the water tank, so that it is possible to detect the water quality even for a low fill level of the water tank.

To charge the capacitor, the water level detection device is advantageously designed to apply a voltage pulse to the electrodes. The voltage pulse decays with the time constant tau=R*C, wherein C is the capacitance of the capacitor and R is the electrical resistance between the electrodes. By applying a voltage pulse, additional switches to enable the capacitor to be charged and discharged are dispensed with.

The water quality and water level detection device is preferably designed to detect the conductivity of the water cyclically. For example, detecting the conductivity can be repeated once a second. It is therefore possible to ensure that the quality of the water is checked at regular intervals during the operation of the water injection device.

To ensure that water is present at the electrodes, the water quality and water level detection device is advantageously set up to determine the conductivity of the water only for a known fill level of the water tank, if the fill level exceeds a predetermined fill level. Thus, on the one hand an unnecessary measurement of conductivity can be dispensed with and on the other hand it can be ensured that the conductivity of the water is actually detected, since the deionized or almost deionized water can have a similar conductivity to the air.

The water quality and water level detection device is preferably set up to determine the fill level before detecting the conductivity. If the determination of the fill level results in the fact that there is enough water for conductivity measurement in the water tank, i.e. that the electrodes are surrounded by water, the conductivity measurement can be carried out.

Alternatively or in addition to the electrochemical sensor, the water quality and water level detection device preferably comprises a first ultrasonic sensor, whereby a density of water can be determined by the ultrasonic sensor for detecting the water quality. This is based on the idea that water of poor quality or other media that can enter the water tank due to faulty filling have a significantly different density than the water of sufficient quality. In this case, the transition time of an ultrasonic signal is preferably measured over a path of known length. From the determined transition time information, the density of the medium and thus a poor water quality can be detected if the density of the water exceeds a predetermined value.

Furthermore, the water quality and water level detection device preferably includes a second ultrasonic sensor. The second ultrasonic sensor is set up to determine the fill level of the water tank for a known density of the water from a transition time of an ultrasonic pulse to the surface of the water and back. The density required to determine the level can particularly preferably be provided by the quality measurement.

Based on the known or recorded density, the speed of sound can be estimated or determined using the distance traveled by the ultrasound taking into account the determined transition time. The distance traveled is an indicator of the fill level of the water tank.

The second ultrasonic sensor is particularly preferably set up to determine the transition time of an ultrasonic pulse from the tank floor to the surface of the water and back. In this case, half of the distance traveled corresponds to the fill level of the water tank. Alternatively, it is possible to determine the transition time of an ultrasonic pulse from the top of the water tank to the surface of the water. The level of the water tank can be calculated from the distance traveled for a known water tank fill height.

In order to allow an even more accurate detection of the fill level of the water tank, the water quality and water level detection device also includes a temperature sensor for recording a temperature of the water, which is taken into account when determining the fill level. As a result, an even more accurate speed of sound can be estimated or determined, as the speed of sound depends on the temperature of the medium through which the ultrasound is propagating. From the determined transition time and the determined speed of sound, the fill level of the water tank is then determined as already described. In this case, the water quality and water level detection device serves as a water quality, water level and temperature detection device.

The second ultrasonic sensor is preferably disposed in the water tank, especially on the tank floor. Thus, the water quality and water level detection device can be designed as a single component in which all sensors are integrated. Alternatively, if the determination of the water level is based on the measurement of the transition time from the top of the tank to the surface of the water, the second ultrasonic sensor may be attached to the top of the tank. This makes it easier to access the second ultrasonic sensor, for example for maintenance work.

Alternatively or in addition, to determine the water level in the water tank, the water quality and water level detection device may preferably include a float element and a sensor, whereby the position of the float element can be determined by means of the sensor. The sensor may be set up to convert the position of the float element into an electrical signal, for example by means of a potentiometric, inductive or magnetostrictive measurement method. Since the float element moves vertically up or down depending on the fill level, the fill level in the water tank can be calculated from the position of the float element.

If the float element is disposed on a lever arm or similar, it is possible to detect the position or angle of the lever arm.

The present disclosure also concerns an internal combustion engine comprising a previously described water injection device. The advantages mentioned with reference to the water injection device are also indicated for the combustion engine.

Another aspect of the disclosure relates to a method for operating a water injection device of an internal combustion engine, whereby the water injection device includes a water tank for storing water. According to the method, a quality of water in the water tank and a fill level of water in the water tank are detected, wherein no water injection is carried out if the detected quality of the water is lower than a predetermined quality and/or the detected fill level of the water tank is less than a predetermined fill level.

A method for operating the previously described water injection device is also disclosed.

BRIEF DESCRIPTION OF THE DRAWINGS

A preferred embodiment of the disclosure is described in detail below, with reference to the accompanying drawing. In the figures.

DETAILED DESCRIPTION

With reference to FIGS. 1 to 7, a water injection device 1 of an internal combustion engine 2 is described in detail in accordance with a preferred embodiment example. In particular, the internal combustion engine 2 is operated according to the Otto principle and with direct gasoline injection.

Figure 1:
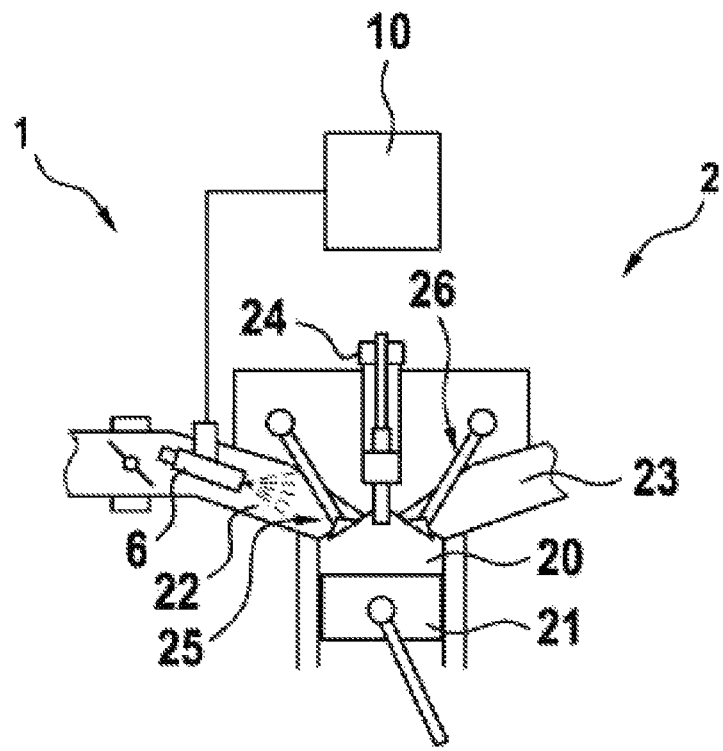
FIG. 1 shows a greatly simplified schematic view of an internal combustion engine with a water injection device according to the preferred exemplary embodiment of the present disclosure.

FIG. 1 shows the internal combustion engine 2, which has a number of cylinders, as well as a part of the water injection device 1 according to the disclosure. The internal combustion engine 2 comprises one combustion chamber 20 per cylinder, in which a piston 21 can be moved back and forth. Furthermore, the internal combustion engine 2 preferably has an inlet channel 22 per cylinder, through which air is supplied to the combustion chamber 20. Exhaust gas is discharged via an exhaust channel 23. For this purpose, an inlet valve 25 is disposed in the inlet channel 22 and an outlet valve 26 is disposed in the exhaust channel 23. Furthermore, the reference character 24 refers to a fuel injection valve.

A water injector 6 is also disposed in the inlet channel 22, which injects water into the inlet channel 22 of the internal combustion engine 2 by means of a control unit 10. In this exemplary embodiment, one water injector 6 per cylinder is provided. Alternatively, two water injectors per cylinder can be arranged for better treatment or to increase the maximum amount of water that can be injected per combustion cycle.

Figure 2:
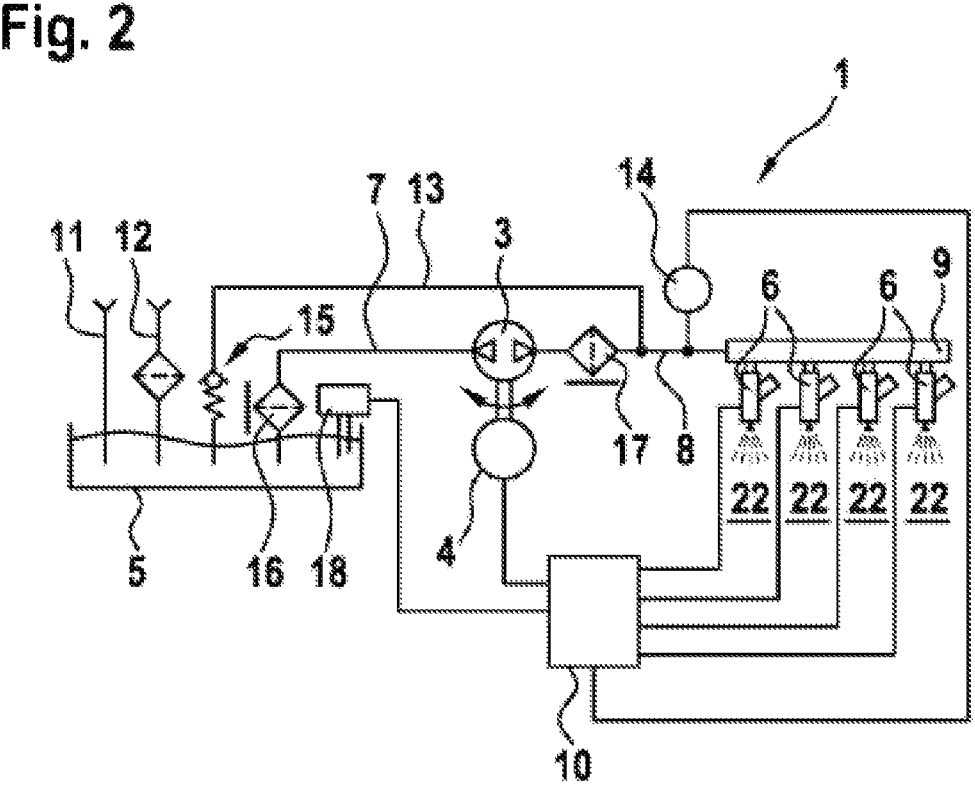
FIG. 2 shows a simplified schematic view of the water injection device according to the preferred exemplary embodiment.

In FIG. 2, the water injection device 1 according to the disclosure is shown in detail. The water injection device 1 preferably includes a conveying element 3 embodied as a pump and an electric drive 4 for driving the conveying element 3. In addition, a water tank 5 is provided, which is connected to the conveying element 3 by an intake line 7. A conveying line 8 connects the conveying element 3 to a distributor 9 or a rail, to which a number of water injectors 6 are connected.

When water injection is needed, water is conveyed from the water tank 5 to the water injectors 6, so that the water is injected into the inlet channels 22 of the internal combustion engine 2.

For this purpose, a condensate of an evaporator that is not shown of an air conditioning system can be used, for which the water injection device 1 according to the disclosure has a feed line 11.

Alternatively or in addition, water can be conveyed into the water tank 5 via a refill line 12. An optional sieve can be provided in the refill line 12. Furthermore, a pre-filter 16 is preferably disposed in the first line 7 and a fine filter 17 is disposed in the second line 8, which can be heated as an option.

To adjust the desired system pressure in the distributor 9, a pressure controller 15, especially in the form of a non-return valve, is disposed in a return line 13 that connects the conveying line 8 to the water tank 5. A pressure sensor 14 in the conveying line 8 is also provided for pressure control.

As already described, if water is refilled via the refill line 12, there is a risk of misuse of the water injection device 1. Accordingly, it is possible that the driver intentionally or accidentally fills the water tank 5 with poor quality tap water, for example with high mineral content, instead of deionized water. Furthermore, when using the condensate from the air conditioning system, there is a risk that the quality is still insufficient for water injection, despite the treatment of the water. Another risk is too low a fill level in the water tank.

These situations can have a negative impact on the readiness of the water injection device 1 to inject water into the internal combustion engine 2 and/or on its quality, as well as on the durability of the components of the water injection device 1 and the internal combustion engine 2.

To prevent this, the water injection device 1 comprises a water quality and water level detection device 18 to detect a quality of water in the water tank 5 and a fill level of the water tank 5.

Preferably, the water quality and water level detection device 18 includes an electrochemical sensor 19 with two electrodes 30 (FIG. 3) disposed in the water tank 5. In this case, a capacitor 31 is connected to one electrode 30. The other electrode 30 is grounded. As a measure of the water quality, a conductivity of the water is used, wherein the detection of the conductivity is based on charging and discharging of the capacitor.

The electrochemical sensor 19 is advantageously disposed in the water tank 5 in such a way that the electrochemical sensor 19 is almost always disposed in the water.

In order to determine the conductivity, a voltage pulse U1 (FIG. 3) is applied to the electrodes 30, via the capacitor (31), especially at a first point in time t1. The voltage pulse U1 corresponds to a first voltage.

Figure 4:
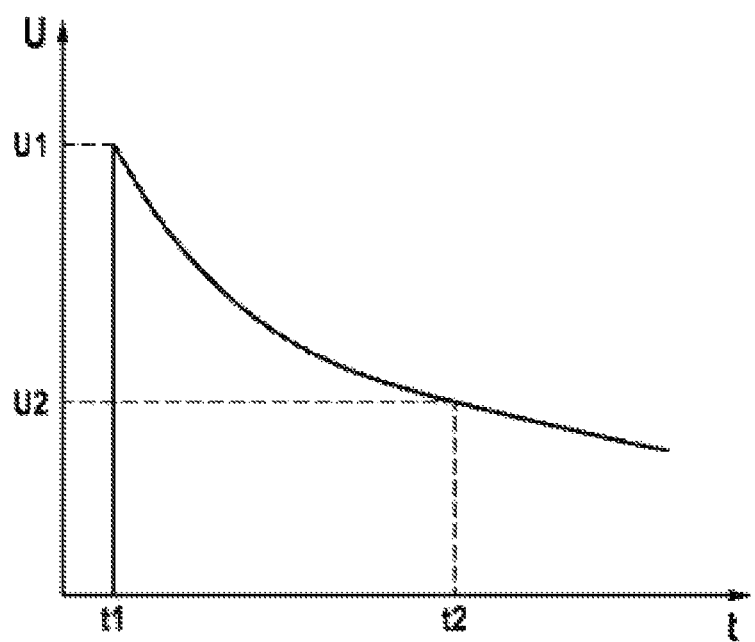
FIG. 4 shows a diagram to explain the detection of the water quality according to the preferred exemplary embodiment.

This process is illustrated in the diagram of FIG. 4. The Y-axis shows a voltage U at the electrodes 30, wherein the time T is shown along the X-axis.

As can be seen from the voltage-time diagram of FIG. 4, the voltage pulse U1 decays with the time constant tau=R*C, wherein R is the electrical resistance between the electrodes 30 and C is the capacitance of the capacitor 31.

The water quality and water level detection device 18 is set up to detect the voltage at the electrodes 30 at a second point in time t2. This voltage corresponds to a second voltage U2.

The step of charging the capacitor 31 is represented by the line perpendicular to the X-axis at the first point in time t1 in the diagram of FIG. 4. The discharging of the capacitor 31 corresponds to the curve from the first point in time t1.

From this curve and the recorded second voltage U2, the electrical resistance R between the electrodes 30 can be determined, wherein the conductivity of the water is calculated by inverting the determined electrical resistance R. A determined conductivity that exceeds a predetermined conductivity means poor water quality or poor quality of the medium in the water tank 5.

Figure 5:
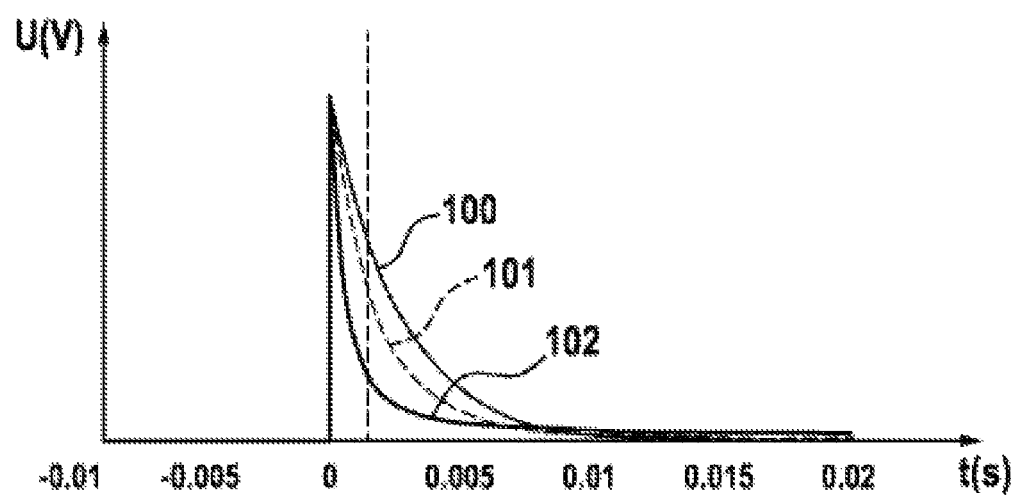
FIG. 5 shows a comparison diagram for water of varying quality that has been recorded according to the preferred exemplary embodiment.

FIG. 5 shows an example of a comparison between curves such as the voltage-time curve of FIG. 4, wherein the curves indicate water of different quality.

For example, the curve 100 corresponds to deionized water, the curve 101 corresponds to water with borderline quality and the curve 112 corresponds to water of poor quality, such as tap water. The voltage is indicated on the Y-axis in V and the time is indicated in s on the X-axis.

Since the conductivity of the air and of deionized water of high quality cannot always be distinguished, it is advantageous if the conductivity measurement is determined only if the fill level is greater than a predetermined fill level.

This ensures that water is present at the electrodes 30 during the conductivity measurement. How the fill level is determined is explained later with reference to FIG. 6.

Figure 3:
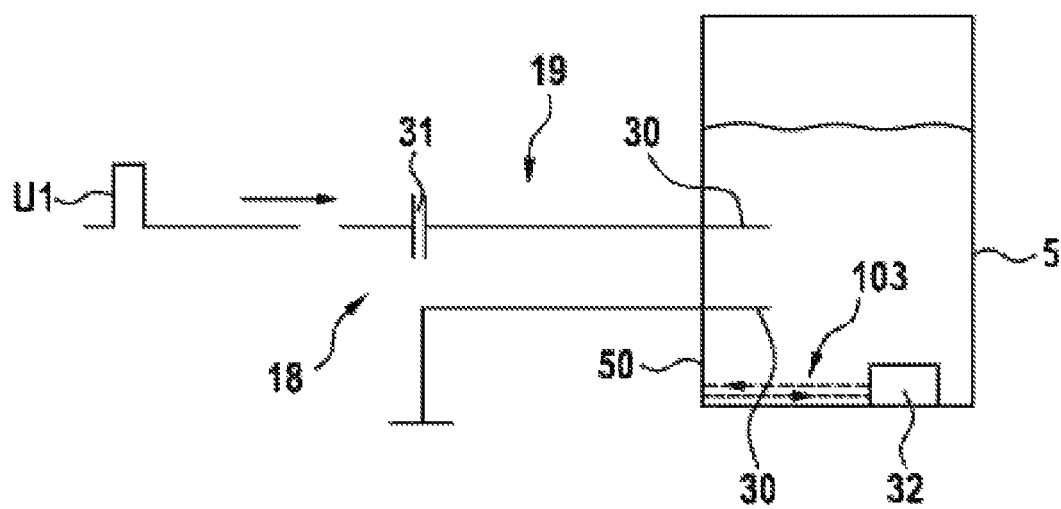
FIG. 3 shows a simplified schematic view of a region of the water injection device according to the preferred exemplary embodiment.

Alternatively or in addition to determining the conductivity of the water, the density of the water can also be measured to detect the water quality. For this purpose, the water quality and water level detection device 18 preferably includes a first ultrasonic sensor (FIG. 3).

In this case, the transition time of an ultrasonic pulse 103 is measured over a path of known length. In FIG. 3, this path is chosen as the distance between the first ultrasonic sensor 32 and a water tank wall 50. The density of the water and thus the water quality can then be determined from the determined transition time. A recorded density greater than a predetermined density suggests poor water quality.

Figure 6:
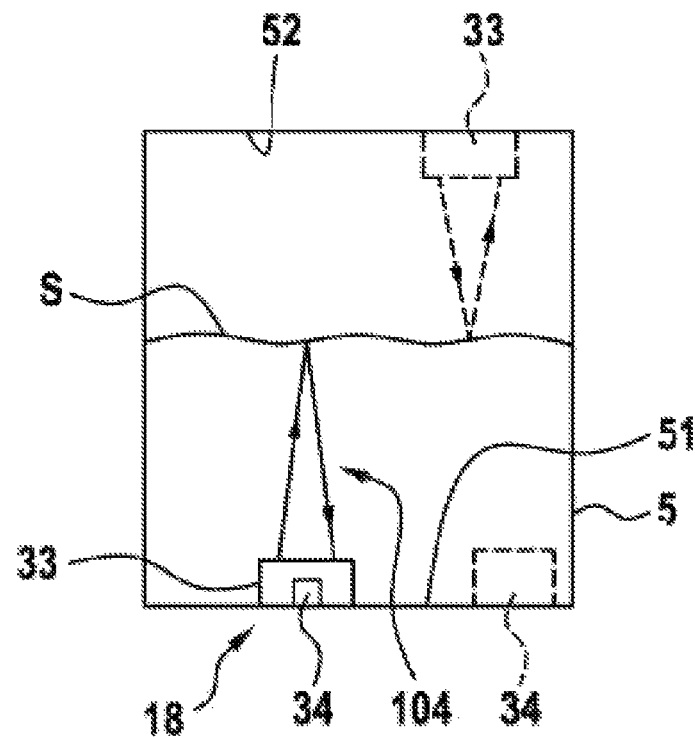
FIG. 6 shows a simplified schematic view of a region of the water injection device according to the preferred exemplary embodiment to explain the detection of the fill level of the water tank.
Figure 7:
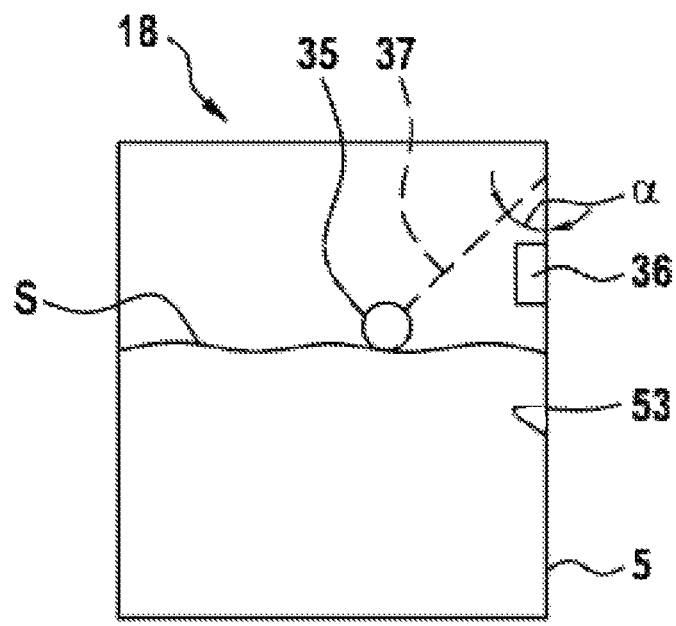
FIG. 7 shows a simplified schematic view of a region of the water injection device to explain an additional or alternative method of detection of the fill level of the water tank.

According to FIG. 6, a second ultrasonic sensor 33 is also preferably provided, which is set up to determine the fill level of the water tank 5 for the known density of the water from a transition time of an ultrasonic pulse up to the surface of the water.

In particular, the second ultrasonic sensor 33 is disposed in a lower region, preferably on the tank floor 51. For example, the fill level S of the water tank 5 is determined from the transition time of an ultrasonic pulse 104 from the tank floor 51 to the water surface and back and the speed of sound in the water. The density determined from the water quality measurement can be used to determine the fill level S or the speed of sound.

In order to achieve an even more accurate measurement of the fill level S, the water quality and water level detection device 18 preferably includes a temperature sensor 34, which is particularly integrated within the second ultrasonic sensor 33. The temperature detected by the temperature sensor 34 is taken into account when calculating the speed of sound in the water.

Advantageously, the electrochemical sensor 19, the first ultrasonic sensor 32, the second ultrasonic sensor 33 and the temperature sensor 34 are integrated into a single component. It is also conceivable that the first ultrasonic sensor 32 and the second ultrasonic sensor 33 are embodied as a single ultrasonic sensor.

Alternatively, the second ultrasonic sensor 33 may be positioned at the top 52 of the water tank 5. In this case, the fill level S of the water tank 5 is from the transition time of the ultrasonic pulse from the top of the water tank 5 to the surface of the water. Thus, the determination of the fill level S is advantageously based on the speed of sound in air and the height (internal dimension) of the water tank. In this case, the temperature sensor 34 is embodied as a separate component. The second ultrasonic sensor 33 and the temperature sensor 34 according to this alternative design are shown dashed in FIG. 6.

Alternatively or in addition, the fill level S can be detected using a float element 35 of a sensor 36. The float element 35 moves vertically up or down depending on the fill level S of the water tank 5. The position of the float element 35 is detected by means of the sensor 36 and is converted into an electrical signal, wherein the detection of the position of the float element 35 is preferably based on a potentiometric and/or magnetostrictive and/or inductive measurement method.

According to an alternative design of the float element 35, a pivoting lever arm 37 is provided, to which the float element 35 is attached. The lever arm 37 is preferably disposed on a tank wall 53. The sensor 36 can detect the position or angle α of the lever arm 37, which determines the fill level S.

The detection of the water quality and/or the water fill level can be carried out cyclically, i.e. at predetermined intervals. For example, the water quality and water level detection facility 18 may be set up for detecting the conductivity and/or the density of the water in the water tank 5 and/or the fill level of the water tank 5

If the detected quality is lower than a predetermined quality and/or the detected water fill level is less than a predetermined water fill level, the water injection is deactivated. In other words, the water injection is deactivated if the detected conductivity of the water exceeds a predetermined conductivity and/or a detected density of water exceeds a predetermined density and/or the recorded water fill level is less than a predetermined water fill level. Deactivation of the water injection means that the control unit 10 is set up to disable the conveying element 3 and/or the water injectors 6 in such a case.

The water quality and water level detection device 18 of the proposed water injection device 1 has the advantages of a combi-detection device or a combi-sensor. The water injection device 1 ensures that no water is used for water injection that is not suitable in terms of quality.

The invention claimed is:

1. A water injection device comprising:
a water tank configured to store water;
a conveying element connected to the water tank and configured to convey water;
at least one water injector connected to the conveying element and configured to inject water; and
a water quality and water level detection device configured to detect a quality of water in the water tank and a fill level of the water tank,
wherein the water quality and water level detection device includes a first ultrasonic sensor, which is configured to determine a density of the water to detect the water quality.

2. The water injection device as claimed in claim 1, wherein:
the water quality and water level detection device includes an electrochemical sensor having two electrodes disposed in the water tank;
a first electrode of the two electrodes is equipped with a capacitor; and
in order to detect the water quality, the water quality and water level detection device is configured to determine a conductivity of the water based on charging and discharging of the capacitor.

3. The water injection device as claimed in claim 2, wherein the water quality and water level detection device is configured to apply a voltage pulse to the two electrodes to charge the capacitor.

4. The water injection device as claimed in claim 2, wherein the water quality and water level detection device is configured to determine the conductivity cyclically.

5. The water injection device as claimed in claim 2, wherein the water quality and water level detection device is configured to determine the conductivity of the water only at a known fill level if the fill level is greater than a predetermined fill level.

6. The water injection device as claimed in claim 1, wherein the water quality and water level detection device includes a second ultrasonic sensor configured to determine the fill level of the water tank for a known density of the water from a transition time of an ultrasonic pulse up to the surface of the water.

7. The water injection device as claimed in claim 6, wherein:
the water quality and water level detection device includes a temperature sensor configured to detect a temperature of the water; and
the temperature of the water is taken into account when determining the fill level.

8. The water injection device as claimed in claim 1, wherein:
the water quality and water level detection device includes a float element and a sensor; and
the sensor is configured to determine a position of the float element.

9. The water injection device as claimed in claim 1, wherein the water injection device is of an internal combustion engine.

10. A water injection device comprising:
a water tank configured to store water;
a conveying element connected to the water tank and configured to convey water;
at least one water injector connected to the conveying element and configured to inject water; and
a water quality and water level detection device configured to detect a quality of water in the water tank and a fill level of the water tank,
wherein the water quality and water level detection device includes a second ultrasonic sensor configured to determine the fill level of the water tank for a known density of the water from a transition time of an ultrasonic pulse up to the surface of the water.

11. A water injection device comprising:
a water tank configured to store water;
a conveying element connected to the water tank and configured to convey water;
at least one water injector connected to the conveying element and configured to inject water; and
a water quality and water level detection device configured to detect a quality of water in the water tank and a fill level of the water tank,
the water quality and water level detection device includes a float element and a sensor; and
the sensor is configured to determine a position of the float element.

* * * * *

UNITED STATES PATENT AND TRADEMARK OFFICE
CERTIFICATE OF CORRECTION

| | |
|---|---|
| PATENT NO. | : 10,890,141 B2 |
| APPLICATION NO. | : 16/473789 |
| DATED | : January 12, 2021 |
| INVENTOR(S) | : Burak et al. |

It is certified that error appears in the above-identified patent and that said Letters Patent is hereby corrected as shown below:

In the Claims

In Claim 11, at Column 8, the phrase --wherein-- should be added in a new line between Lines 61 and 62.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*